United States Patent
Pannetier-Lecoeur et al.

(10) Patent No.: US 10,363,128 B2
(45) Date of Patent: Jul. 30, 2019

(54) DEVICE AND METHOD FOR PROSTHETIC REHABILITATION OF THE RETINA

(71) Applicant: COMMISSARIAT A L'ENERGIE ATOMIQUE ET AUX ENERGIES ALTERNATIVES, Paris (FR)

(72) Inventors: Myriam Pannetier-Lecoeur, Bures-sur-Yvette (FR); Vincent Trauchessec, Antony (FR); Laure Caruso, Paris (FR); Frederic Chavane, Marseilles (FR); Sebastien Roux, La Ciotat (FR); Frederic Matonti, Marseilles (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 15/546,921

(22) PCT Filed: Jan. 26, 2016

(86) PCT No.: PCT/FR2016/050156
§ 371 (c)(1),
(2) Date: Jul. 27, 2017

(87) PCT Pub. No.: WO2016/120557
PCT Pub. Date: Aug. 4, 2016

(65) Prior Publication Data
US 2017/0367813 A1 Dec. 28, 2017

(30) Foreign Application Priority Data
Jan. 28, 2015 (FR) ..................................... 15 50639

(51) Int. Cl.
*A61F 2/16* (2006.01)
*A61F 2/14* (2006.01)
(Continued)

(52) U.S. Cl.
CPC .............. *A61F 2/1451* (2015.04); *A47G 1/22* (2013.01); *A61F 9/00727* (2013.01);
(Continued)

(58) Field of Classification Search
CPC .. A61F 2/1451; A61F 2/14; A61F 9/08; A61F 9/00727; A61F 2250/0002;
(Continued)

(56) References Cited

U.S. PATENT DOCUMENTS 5,147,284 A * 9/1992 Fedorov .................... A61F 2/14
600/14
6,511,508 B1 * 1/2003 Shahinpoor ............. A61F 2/147
600/37
(Continued)

FOREIGN PATENT DOCUMENTS

ES 2370014 A1 12/2011
FR 2 673 481 A1 9/1992
(Continued)

OTHER PUBLICATIONS

Basham, E., et al., "Functional Magnetic Stimulation for Implantable Epiretinal Prosthesis," ARVO Annual Meeting Abstract, May 2005, 1, page.
(Continued)

*Primary Examiner* — David H Willse
*Assistant Examiner* — Tiffany Shipmon
(74) *Attorney, Agent, or Firm* — Pillsbury Winthrop Shaw Pittman LLP (57) ABSTRACT

A device for prosthetic vision rehabilitation, which includes a scleral explant with a shape that is suitable for being in contact with at least one portion of the sclera of an eye, and at least one inducer arranged on the scleral explant.

8 Claims, 9 Drawing Sheets

(51) Int. Cl.
*A61F 9/007* (2006.01)
*A61N 1/05* (2006.01)
*A47G 1/22* (2006.01)
*F16B 15/00* (2006.01)
*A61N 5/06* (2006.01)
*A61N 1/36* (2006.01)
*A61N 1/40* (2006.01)

(52) U.S. Cl.
CPC ........ *A61N 1/0543* (2013.01); *F16B 15/0023* (2013.01); *A61F 2250/0002* (2013.01); *A61N 1/36046* (2013.01); *A61N 1/40* (2013.01); *A61N 5/0622* (2013.01)

(58) Field of Classification Search
CPC .............. A61N 1/0543; A61N 1/36046; A61N 5/0622; A61B 90/36
USPC ...................................................... 607/53–54
See application file for complete search history.

(56) References Cited

U.S. PATENT DOCUMENTS

| | | | | |
|---|---|---|---|---|
| 7,483,750 | B2* | 1/2009 | Greenberg | A61F 9/0017 607/54 |
| 7,967,439 | B2* | 6/2011 | Shelhamer | A61B 3/113 351/209 |
| 8,313,375 | B2* | 11/2012 | Yoro | G06F 3/0482 345/173 |
| 2002/0038134 | A1* | 3/2002 | Greenberg | A61N 1/0543 607/1 |
| 2006/0271123 | A1* | 11/2006 | Greenberg | A61N 1/36046 607/53 |
| 2009/0076367 | A1* | 3/2009 | Sit | A61B 3/16 600/398 |
| 2013/0150699 | A1* | 6/2013 | Ostermeier | A61B 3/16 600/398 |
| 2013/0178907 | A1* | 7/2013 | Ok | A61F 15/001 607/2 |
| 2013/0178933 | A1 | 7/2013 | Serrano Olmedo et al. | |
| 2014/0371565 | A1* | 12/2014 | Glasser | A61N 1/36046 600/383 |
| 2018/0092738 | A1* | 4/2018 | Tai | A61F 2/1613 |

FOREIGN PATENT DOCUMENTS

| | | |
|---|---|---|
| WO | WO 00/74600 A1 | 12/2000 |
| WO | WO 2013/126498 A1 | 8/2013 |

OTHER PUBLICATIONS

International Preliminary Report on Patentability and the Written Opinion of the International Searching Authority as issued in International Patent Application No. PCT/FR2016/050156, dated Aug. 1, 2017.

International Search Report as issued in International Patent Application No. PCT/FR2016/050156, dated Mar. 23, 2016.

* cited by examiner

DEVICE AND METHOD FOR PROSTHETIC REHABILITATION OF THE RETINA

CROSS-REFERENCE TO RELATED APPLICATIONS

This is U.S National Stage of PCT/FR2016/050156, filed Jan. 26, 2016, which in turn claims priority to French Patent Application No. 1550639, filed Jan. 28, 2015, the entire contents of all applications are incorporated herein by reference in their entireties.

TECHNICAL FIELD OF THE INVENTION

The technical field of the invention is that of the prosthetic rehabilitation of the retina. The present invention relates to a device and a method for prosthetic rehabilitation of the retina. An important application of the invention relates to the treatment of diseases of the retina of degenerative retinopathy or age-related macular degeneration (AMD) type.

TECHNOLOGICAL BACKGROUND OF THE INVENTION

Retinal degeneration, such as age-related macular degeneration (AMD) and retinitis pigmentosa, currently affects a large portion of the worldwide population, a proportion that is increasing with the ageing of the population.

One avenue explored for treating these pathologies is to carry out an artificial stimulation of the ganglionic neurons with the aim of transferring through the optic nerve a signal that can be used by the visual system.

Such a neuronal stimulation or activation may be artificially induced by pharmacological means or by direct electrical excitation by applying a potential difference on the neuron or the set of neurons to excite.

In the case of a stimulation by pharmacological means, the response and the recovery time may be quite slow, on account of the diffusion time of the pharmacological agent up to the zone of interest. Conversely, electrical stimulation is very rapid, but necessitates an electrical contact with the neuron or the zone to excite. The electrical contact may be made by physical contact of a conductor with the actual neuron or the zone to excite, or by placing a conductor in the immediate vicinity of the neuron or the zone to excite, given the conductivity of the tissues that surround the neuron or the zone to excite.

Artificial electrical retina devices are thus known which comprise systems of implanted microelectrodes in contact with the region to excite. Electrical pulses are delivered by means of an external generator on a number of microelectrodes typically comprised between several tens and several hundreds.

Nevertheless, this technique has certain limitations. A first limitation is due to diffusion of the electrical current in the tissues around the targeted region. In particular, neurons not targeted by the stimulation may be activated via their axon passing in the stimulated region. The spatial selectivity of the excitation and the efficiency of the excitation on the focused zone are thus greatly limited.

A second limitation is linked to the necessity of positioning the implant as near as possible to the neurons to excite, which involves complex and risky implantation surgery. Indeed, whatever the type of prosthesis employed, their positioning has to be done in direct contact with the retina, which imposes potentially impairing sub-or epi-retinal surgery. This mode of implantation in direct contact with the retina also limits the dimensions of the implant to lateral dimensions of the order of 3 mm sides if the implant has a square surface, or 3 mm diameter if the implant has a round surface. At such dimensions, the deformation due to the curvature of the eye is very small, but the implant can thus only activate a very limited portion of the total surface of the retina. Finally, the reaction of the tissues to the presence of the implant may lead in the medium and long term to the development, by an inflammatory reaction and cicatrisation, of granulation tissues, which, in covering the microelectrodes, considerably decrease their efficiency by insulating the microelectrode-tissue interface. This problem is common to implants based on electrical stimulation, such as deep cerebral stimulation implants, or cortical implants within the framework of brain-machine interfaces for example.

It is also known to induce neuronal activation using a magnetic field pulse. Indeed, a rapid variation of magnetic field, created for example by a current pulse in a coil, generates an electric field according to Faraday's law:

$$\nabla \times E = -\frac{\partial B}{\partial t}.$$

The interest of the use of the magnetic field pulse on one or more neurons, in terms of clinical application, is linked to the possibility of stimulation of neurons at a distance. Thus, depending on the geometry of the winding, it is possible to create an activation zone at a distance from the exciter coil, and to activate or to inhibit neurons without physical contact therewith, or even with the tissues surrounding them.

At a macroscopic level, this principle is used to stimulate populations of neurons at the scale of the cortical zones of the brain; it is designated Transcranial Magnetic Stimulation. This technique uses large coils with a lateral dimension of 10 to 30 centimeters, in which a current pulse is applied, leading to a rapid variation of the magnetic field and thus the creation of an electric field on a zone of the brain selected by the emplacement and the geometry of the coils. The coils used in transcranial magnetic stimulation are typically planar multi-turn coils, with generally between 10 and 30 turns, of circular, square or rectangular shape. The dimensions of such a coil are typically of the order of 5 to 15 cm side or diameter. Two adjacent coils are generally used in transcranial magnetic stimulation techniques. It has been shown that this technique makes is possible either to activate or to inhibit a neuronal population, as a function of the polarity of the field E with respect to the population. This macroscopic technique is used within the framework of research in cognitive sciences on healthy or pathological brains, as well as in the treatment of psychiatric disorders, for example on depressions resistant to medical treatments.

The document "Functional Magnetic Stimulation for Implantable Epiretinal Prosthesis", by E. Basham, M. Sivaprakasam and W. Liu (2005) suggests, in order to restore the vision of patients suffering from retinitis pigmentosa or age-related macular degeneration, using magnetic stimulation while pointing to the advantages in terms of biocompatibility and bioresistance compared to electrical stimulation. However, the problem of the complexity of the implantation surgery of such implants remains.

SUMMARY OF THE INVENTION

The invention offers a solution to the problems evoked previously by proposing a device for prosthetic vision rehabilitation enabling an implantation surgery that is simplified with respect to the known prior art.

One aspect of the invention thus relates to a device for prosthetic vision rehabilitation, which comprises:
- a scleral explant with a shape that is suitable for being in contact with at least one portion of the sclera of an eye, and
- at least one inducer arranged on the scleral explant.

Thanks to the invention, a scleral explant is used comprising at least one inducer to enable an excitation at a distance of ganglionic neurons, the scleral explant being able to be arranged on the sclera of an eye thanks to a simplified implantation surgery, which is more rapid and less risky than in the prior art, The device for prosthetic vision rehabilitation according to one aspect of the invention thus has the advantage of being less invasive than devices of the prior art.

Apart from the characteristics that have been evoked in the preceding paragraph, the prosthetic rehabilitation device according to one aspect of the invention may have one or more additional characteristics among the following, considered individually or according to all technically possible combinations thereof:

The at least one inducer is capable of creating an electromagnetic field for neuronal stimulation of an excitation zone, while being galvanically insulated from said excitation zone, The invention thus advantageously enables a stimulation of an excitation zone without irritation or inflammatory reaction or cicatrisation of said excitation zone, and thus the lengthening of the lifetime of the explant.

The scleral explant has a spherical calotte shape. The scleral explant is thus advantageously capable of being arranged in contact with at least one portion of the sclera of an eye. The scleral explant of the invention advantageously makes it possible to cover a retinal zone much more extended than during the use of a sub-retinal or epi-retinal implant. In particular, the spherical calotte may be a hemisphere.

The scleral explant comprises a central portion and a peripheral portion surrounding the central portion, and the at least one inducer is arranged on the peripheral portion of the scleral explant.

According to a first embodiment of the invention, the scleral explant comprises an opening. The scleral explant according to the first embodiment of the invention may thus advantageously be arranged at the back of an eye, the passage of the optic nerve of the eye being provided through the opening. The opening is advantageously arranged in the central portion of the scleral explant.

According to the first embodiment of the invention, the scleral explant comprises a slit arranged between an external periphery of the scleral explant and the opening of the scleral explant, the slit defining two ends of the scleral explant being able to be moved apart from one another. The slit of the scleral explant advantageously contributes to facilitating the layout of the scleral explant on an eye, particularly during a configuration of the scleral explant at the back of an eye. Indeed, by moving the two ends of the sclera explant apart, on either side of the slit, the passage is enabled of an optic nerve of an eye of which it is wished to restore vision.

According to an alternative of the first embodiment of the invention, the scleral explant has a system for attaching the two ends of the scleral explant. The attachment system of the scleral explant advantageously makes it possible to close up the scleral explant again, typically after having made the scleral explant pass under the extra-ocular muscles and enables the passage of the optic nerve in the opening of the scleral explant.

The device for prosthetic vision rehabilitation comprises a plurality of inducers arranged on the scleral explant. The positioning and the spacing of each inducer with respect to other inducers of the plurality of inducers is advantageously calculated to assure the independence of each inducer.

Another aspect of the invention relates to a system for prosthetic vision rehabilitation, which comprises:
- an image acquisition unit;
- an image processing unit, receiving as input an image acquired by the image acquisition system and sending back as output an encoding of said image;
- a control unit, receiving as input the encoding of said image and sending back as output a command for a pulse generator;
- the pulse generator, sending according to the command of the control unit at least one pulse to a multiplexer;
- the multiplexer, transmitting the at least one pulse to the at least one inducer or to at least one portion of the plurality of inducers of a device for prosthetic vision rehabilitation according to one aspect of the invention.

The invention and the different applications thereof will be better understood on reading the description that follows and by examining the figures that accompany it.

BRIEF DESCRIPTION OF THE FIGURES

The figures are presented for indicative purposes and in no way limit the invention.

FIG. 7b schematically shows the magnetic field focal point obtained with a second configuration of the array of inducers of FIG. 7a.

FIG. 7c schematically shows the magnetic field focal point obtained with a third configuration of the array of inducers of FIG. 7a.

DETAILED DESCRIPTION OF AT LEAST ONE EMBODIMENT OF THE INVENTION

Unless specified otherwise, a same element appearing in the different figures has a single reference.

Figure 1A:
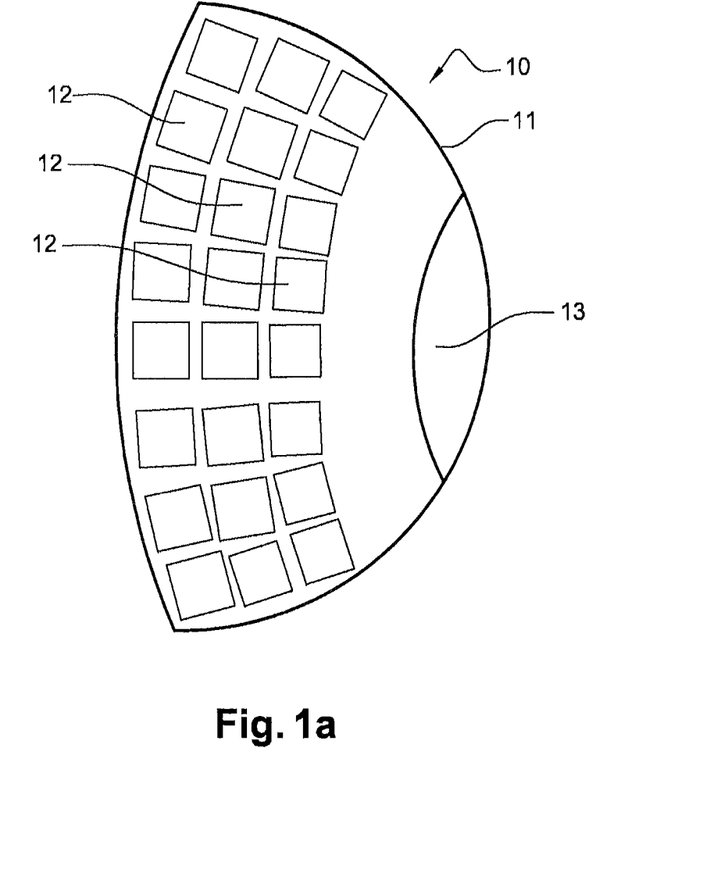
FIG. 1a schematically shows a first view of a device for prosthetic vision rehabilitation according to a first embodiment of the invention.
Figure 1B:
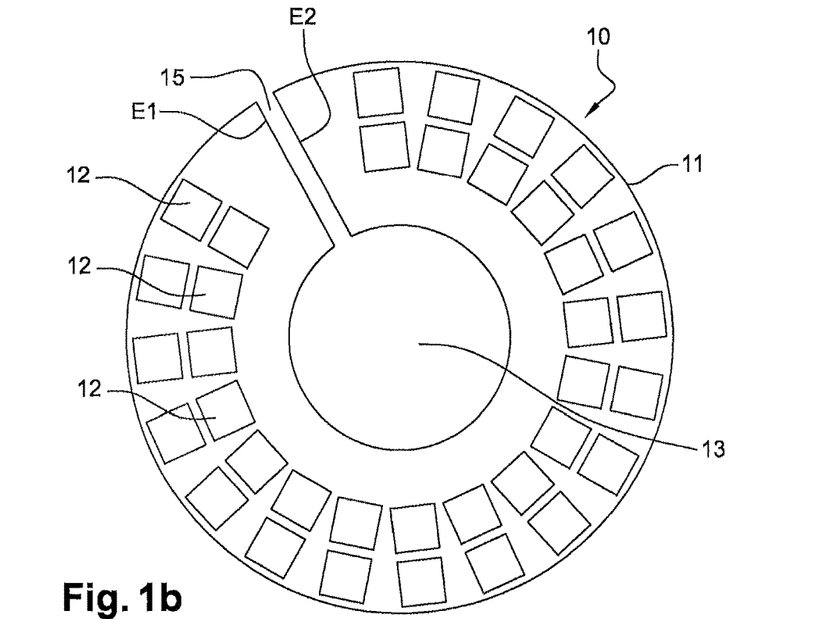
FIG. 1b schematically shows a second view of the device for prosthetic vision rehabilitation according to the first embodiment of the invention.
Figure 1C:
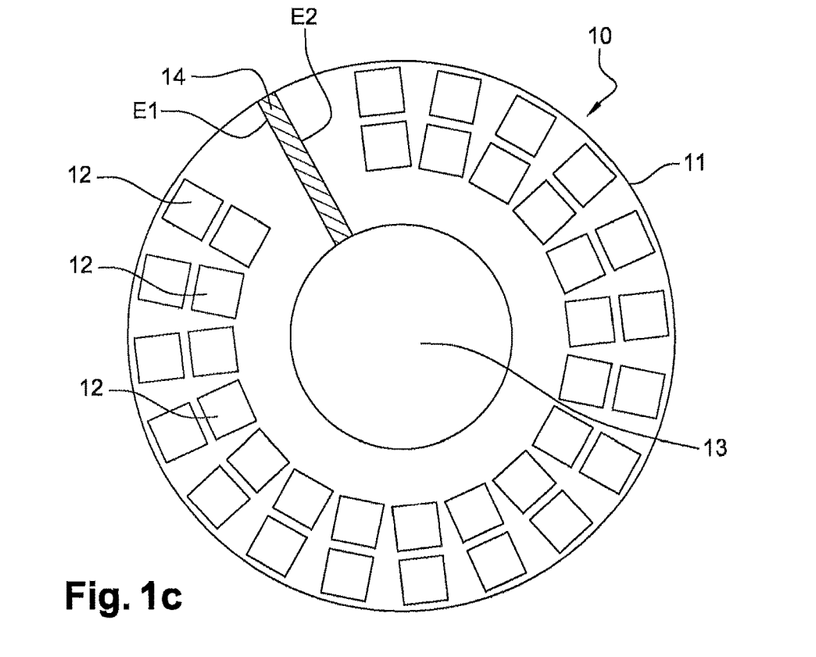
FIG. 1c schematically shows a view of the device for vision rehabilitation according to an alternative of the first embodiment of the invention.

FIG. 1a schematically shows a first side view of a device 10 for prosthetic vision rehabilitation according to a first embodiment of the invention. FIG. 1b schematically shows a second rear view of the device 10 for prosthetic vision rehabilitation according to the first embodiment of the invention. FIG. 1c schematically shows a rear view of an alternative of the device 10 for prosthetic vision rehabilitation according to the first embodiment of the invention, according to which the device 10 comprises an attachment system 14. FIGS. 1a, 1b and 1c are described jointly.

The device 10 for prosthetic vision rehabilitation according to the first embodiment of the invention comprises:
  a scleral explant 11 with a shape that is suitable for being in contact with at least one portion of the sclera of an eye, and
  a plurality of inducers 12 arranged on the scleral explant 11.

The sclera is a protective membrane of the eye. According to the first embodiment of the invention, the sclera explant 11 advantageously comprises an opening 13. The opening 13 is dimensioned to enable the passage of an optic nerve. The sclera explant 11 is thus suitable for being in contact with at least one portion of the sclera of an eye, the optic nerve of the eye passing through the opening 13. According to the first embodiment of the invention, the scleral explant 11 advantageously comprises a slit 15, or cut, made between the outer periphery of the scleral explant 11 and the opening 13 of the scleral explant 11. The slit 15 defines a first end E1 and a second end E2 of the scleral explant 11, on either side of the slit 15. The first and second ends E1 and E2 of the scleral explant 11 may be moved away from each other to make it possible to slide the scleral explant 11 under the extra-ocular muscles of an eye, and to enable the passage of an optic nerve and the layout of the optic nerve in the opening 13 of the scleral explant 11. The slit 15 thus advantageously makes it possible to facilitate the putting in place of the scleral explant 11 on the rear face of an eye of which it is wished to restore vision. When no stress is exerted thereon, the first and second ends E1 and E2 of the scleral explant 11 are typically situated facing each other, aligned with each other. The attachment system 14 according to the alternative of the first embodiment of the invention represented in FIG. 1c advantageously makes it possible to attach the first and second ends E1 and E2 to each other to prevent them from moving away from one another. Thus, typically after having moved the first and second ends E1 and E2 of the scleral explant 11 away from each other to enable the passage of the optic nerve, the scleral explant 11 may be closed up again in a robust manner.

The scleral explant 11 according to the first embodiment of the invention is intended to be arranged on the sclera covering the external face of the eye, at the back of the eye. Such a positioning of the scleral explant 11 may be obtained thanks to surgery that is simple and not very invasive consisting in inserting the scleral explant 11 through an incision made in the conjunctiva. A particular example of surgical operating mode will be detailed hereafter in the present document. An important advantage of the first embodiment of the invention is to enable a large coverage of the retina and an excitation of neurons over a maximum surface, covering a wide visual field, unlike devices according to the prior art which only use a small stimulation zone.

Figure 2:
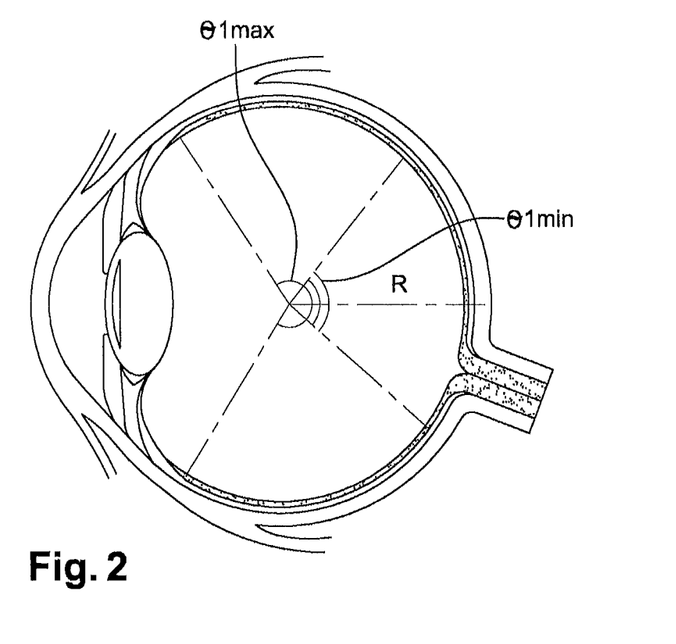
FIG. 2 schematically shows different dimensioning parameters of the device for prosthetic vision rehabilitation according to the first embodiment of the invention.

In the particular example illustrated in FIGS. 1a to 1c, the scleral explant 11 thus has a pierced lens shape, adapted to the natural curvature of the sclera, The scleral explant 11 may also be described as being a spherical calotte, the dimensions of which are chosen to enable the adaptation of the scleral explant 11 on an eye. An eye typically being able to be likened to a sphere having a diameter of the order of 23.5 mm, the spherical calotte is preferentially defined from a sphere S having a radius R comprised between 10 mm and 14 mm and typically equal to 12 mm, the spherical calotte being limited by the intersection with the sphere S of a first cone of revolution C1 with as summit the centre of the sphere S and with half-angle at the summit θ1 comprised between 45° and 110°. In particular, the spherical calotte may be a hemisphere. FIG. 2 schematically shows an eyeball and illustrates the manner in which the parameters R and θ1 are defined.

Given the dimensions of an optic nerve and its emplacement on an eyeball, the opening 13 advantageously has a diameter comprised between 2 mm and 6 mm, and preferentially a diameter of 3 mm. It involves, in a general manner, enabling the passage of the optic nerve through the opening 13 without contact or rubbing between the optic nerve and the scleral explant, while having a maximum coverage of the foveal region, the fovea being typically situated at around 2 mm from the optic nerve. In the particular example where the opening 13 has a diameter of 10 mm, the opening 13 is advantageously defined by a second cone of revolution C2 with same generating line as the first cone of revolution C1 and with as summit the centre of the sphere S. In the particular example where the opening 13 has a diameter of 2 mm, the opening 13 is advantageously defined as a function of the precise positioning of the optic nerve of the eyeball.

Figure 3:
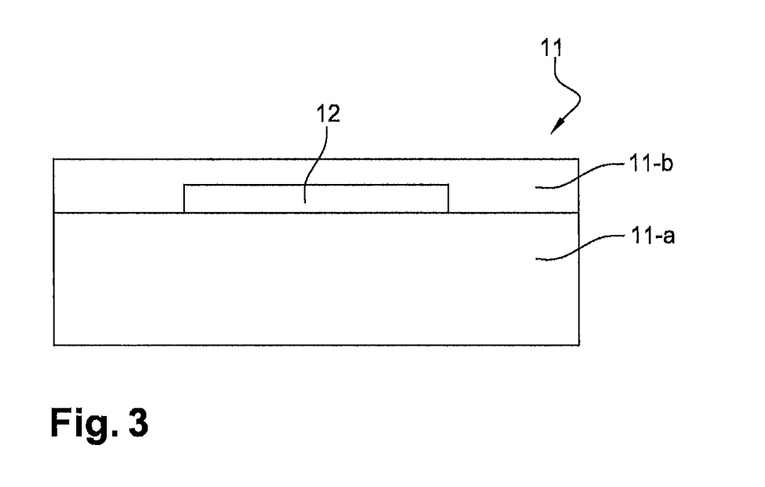
FIG. 3 schematically shows a partial view in section of a device for prosthetic vision rehabilitation according to one aspect of the invention.

FIG. 3 schematically shows a partial view in section of a device 10 for prosthetic vision rehabilitation according to one aspect of the invention. FIG. 3 shows in particular that the scleral explant 11 comprises:
  a substrate 11-a, on the surface of which is arranged an inducer 12, and an insulating layer 11-*b*, which is deposited on the inducer 12 and on the portion of the substrate 11-*a* which is not covered by the inducer 12.

The substrate 11-*a* is made of an insulating material, such as for example Kapton, glass, polyimide, Parylene, silicone or silicone-hydrogel.

The inducer 12 is made of a conductive material, such as for example copper, gold or an assembly of several materials. The inducer 12 is preferentially made of copper, which has a high conductivity, potentially covered by a layer of gold or tantalum, for example deposited by sputtering, evaporation or chemical deposition, in order to avoid oxidation of the copper in the long term. The inducer 12 is advantageously produced by a micro-machining technique or by a micro-fabrication technique. In the case where the inducer 12 is produced by a micro-machining technique, the inducer 12 is advantageously produced by laser micro-machining in a conductive layer of several pm to several tens of pm thickness, and preferentially of 1 µm to 20 µm thickness, the conductive layer being for example deposited on the substrate 11-*a* by electrodeposition. In the case where the inducer 12 is produced by a micro-fabrication technique, the inducer 12 is advantageously produced by chemical or dry etching of a conductive layer deposited on the substrate 11-*a* by evaporation, by cathodic sputtering or by electrodeposition, through a resin mask obtained by a lithographic process in order to obtain a spatial resolution of the inducer 12 of the order of a pm. It is also possible to produce the inducer 12 by a process of electrodeposition through a resin mask. Compared to micro-machining, micro-fabrication makes it possible to obtain more precise patterns and of smaller size for the inducer 12, which is advantageous for integrating a greater number of inducers on the surface of the substrate 11-*a*. The thickness and the width of the inducer 12 are chosen in order to enable the passage of the current necessary for the generation of a magnetic field enabling the excitation of a zone of neurons, while avoiding any damage for the surrounding tissues. The inducer 12 typically has a lateral dimension of around 500 µm.

The insulating layer 11-*b* that is deposited on the inducer 12 has a thickness that is chosen as a function of the dielectric constant of the material of the insulating layer 11-*b*, to make it possible to limit considerably any capacitive coupling of the inducer 12 with the tissues. The material of the insulating layer 11-*b* is chosen to be biologically compatible, in order to avoid an inflammatory reaction of the tissues. An insulating layer 11-*b* made of an alumina/silicon nitride bi-layer of 1 µm thickness makes it possible for example to reduce considerably any capacitive coupling while assuring a long term performance of the scleral explant 11. More generally, the thickness of the insulating layer 11-*b* is typically comprised between 1 µm and 20 µm. The insulating layer 11-*b* may be a polymer film. The insulating layer 11-*b* may be an oxide film of $Al_2O_3$, $SiO_2$, $Si_3N_4$ type or a combination of these materials.

Figure 4A:
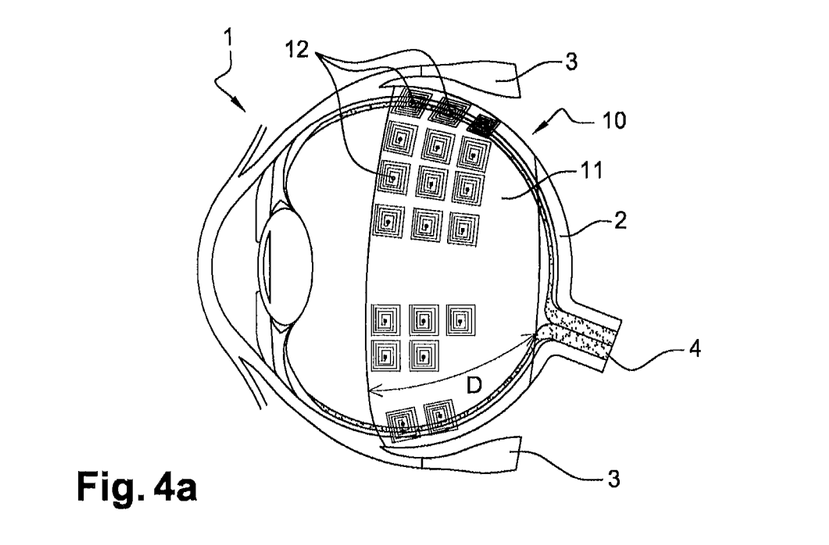
FIG. 4a schematically shows a first view of the device for prosthetic vision rehabilitation according to the first embodiment of the invention, arranged in contact with a portion of the sclera of an eye.
Figure 4B:
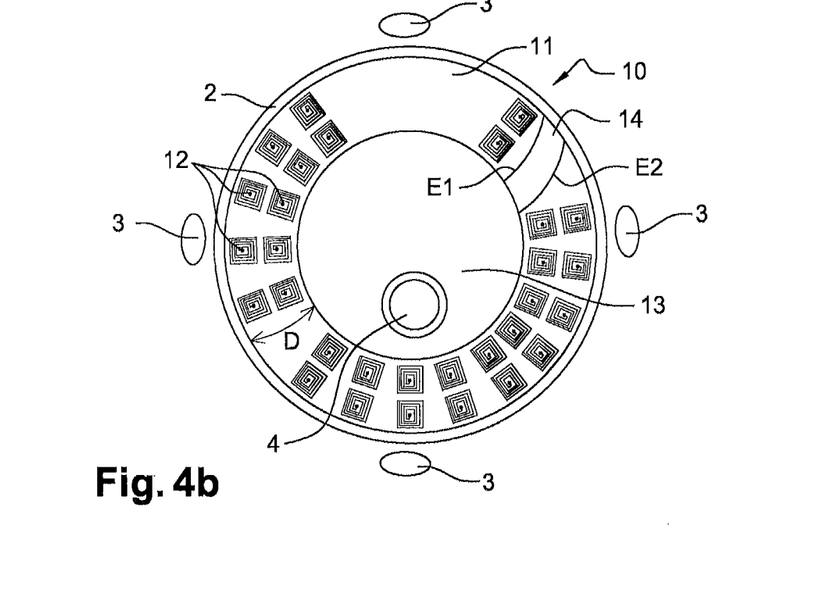
FIG. 4b schematically shows a second view of the device for prosthetic vision rehabilitation according to the first embodiment of the invention, arranged in contact with a portion of the sclera of an eye.

FIG. 4*a* schematically shows a first view of the device 10 for prosthetic vision rehabilitation according to the first embodiment of the invention, arranged in contact with a portion of the sclera 2 of an eye 1. FIG. 4*b* schematically shows a second view of the device 10 for prosthetic vision rehabilitation according to the first embodiment of the invention, arranged in contact with a portion of the sclera 2 of the eye 1. FIGS. 4*a* and 4*b* are described jointly.

FIGS. 4*a* and 4*b* show the eye 1, the sclera 2, the extra-ocular muscles 3 and the optic nerve 4. The device 10 for prosthetic vision rehabilitation is arranged in contact with a portion of the sclera 2 of the eye 1, the scleral explant 11 having a lens, or spherical calotte, shape, the curvature of which is adapted to the curvature of the sclera 2. The opening 13 of the scleral explant enables the passage of the optic nerve 4. FIG. 4*b* shows in particular the attachment system 14 of the scleral explant 11, according to the alternative of the first embodiment of the invention. The attachment system 14 may for example be formed thanks to a system of loops, cradles, sleeves or clips, and preferentially thanks to a system of clips or cradles given the typical dimensions of the scleral explant 11.

A mode of surgical implantation of the scleral explant 11 of the device 10 for prosthetic vision rehabilitation according to the first embodiment of the invention is now described. Under loco-regional or general anaesthetic, conjunctival disinsertion by peritomy at the fornix, putting in place draw threads on the four oculomotor rectus muscles, exposure of the scleral surface in the four inter-muscular quadrants, passage of the sclera explant 11 under the rectus muscles and suture of the scleral explant 11 to the sclera by non-absorbable episcleral stitches in order to assure the stability of the scleral explant 11, then closing of the conjunctiva by limbal stitches with absorbable thread. This example of mode of surgical implantation does not comprise a step of opening of the ocular wall and thus eliminates any endo-ocular infection risk. The scleral explant 11 being intended to be arranged in contact with the sclera, and not in direct contact with the retina, the risks of trauma or retinal detachment are avoided. The surgical implantation of the scleral explant according to one aspect of the invention may thus be carried out by means of a short surgery, that is to say of less than one hour, being able to take place in outpatient care. As a comparison, an epi-retinal surgical implantation necessitates an intervention of around 3 h, and a sub-retinal surgical implantation necessitates for its part an intervention of more than 6 h, with hospitalisation. The device 10 for prosthetic vision rehabilitation according to the first embodiment of the invention thus advantageously enables an implantation surgery that is much less invasive, much less risky and markedly shorter than epi-retinal or sub-retinal device implantation surgeries according to the prior art.

Figure 5:
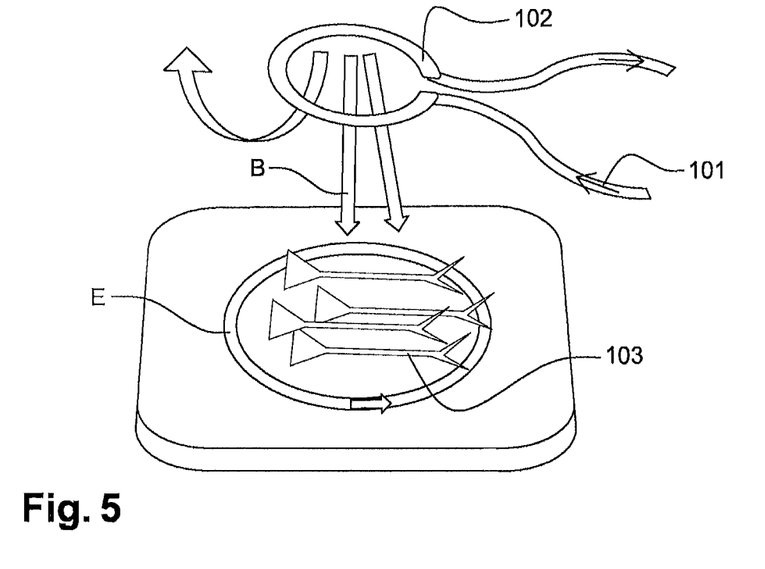
FIG. 5 schematises the physical principle of neuronal activation by an electromagnetic pulse of a device for prosthetic vision rehabilitation according to one aspect of the invention.

FIG. 5 shows the physical principle of neuronal activation of at least one neuron of a target zone by a contact-free electromagnetic pulse, the physical principle that is applied by the present invention. An electromagnetic signal is created by the passage of a current pulse 101 in a conductor 102, or inducer. The current pulse 101 is intense and of short duration. The conductor 102 is for example obtained by physical winding or by micro-fabrication means, such as an etching or a deposition of thin films. The conductor 102 is galvanically insulated from its environment by an insulating sheath or insulating film. In the present document, "the conductor 102 is galvanically insulated from its environment" is taken to mean the fact that there is no electrical contact between the conductor 102 and its environment.

The electromagnetic signal created under the effect of the passage of the current pulse 101 in the conductor 102 has a magnetic component B that depends on the amplitude of the current pulse 101 and the geometry of the conductor 102. The amplitude of the electromagnetic signal typically decreases as the inverse of the distance travelled by said electromagnetic signal. In a conductive medium such as that of tissues, the variation in magnetic field B is associated with an electric field E, which propagates in said conductive medium. The electric field E then acts on at least one neuron 103 leading to an activation of said at least one neuron 103 by transmembrane depolarisation. The activation or the inhibition of at least one neuron 103 is notably conditioned by:
- the value of the field B and the variation in the field B over time, in order to reach a neuronal activation threshold value,
- the orientation of the current pulse 101 with respect to the axis of the at least one neuron 103 to activate,
- the spatial distribution of the field E created, and in particular the gradient of the field E created, which is an important parameter of membrane depolarisation or hyperpolarisation leading to activation or inhibition of the neuron.

Thus, in the ideal case where the component of the electric field E along a perfectly straight neuronal component, such as a dendrite or an axon, has a positive gradient, the membrane of the neuron hyperpolarises, whereas with a negative gradient, the membrane of the neuron depolarises. However, in tissues, neurons have non-ideal morphologies and the application of a variable magnetic field B of sufficient intensity enables an activation of the neuronal tissues for different orientations of the applied field.

More generally, the intensity of the magnetic field required for the activation of a neuron by an inducer varies with the distance separating the inducer from the neuron. Thus, in transcranial magnetic stimulation, the distance separating the inducer from the neuron is of the order of 1 to 6 cm and the magnetic fields delivered correspond to threshold electric fields E of around 100V/m. For a local stimulation at around 1 mm distance and less, the thresholds reached are then around 5V/m. It is thus advantageous to bring the inducer or the inducers closer to the neuron or neurons to excite in order to reach the activation threshold with a current not generating heating incompatible with the implantation of the inducer or inducers. A planar coil comprising a single turn may be used, but in order to increase the value of the magnetic field generated, it is advantageous to increase the number of turns of the coil, either by creating concentric turns, or by depositing two turns on either side of a substrate and connecting them. The two techniques may be combined. The design of the turn is chosen as a function of the desired dimensions for the inducer and the width of the tracks, while making sure to minimise the resistance of the inducer to values of the order of several Ohms. Thus, for a coil of 400 μm external radius produced in a layer of copper of 10 μm, a series of 10 concentric turns of 10 μm unit width will typically lead to a resistance of around 3 Ohms and will deliver a field B at 600 μm of 1.5 mT for 1 A of current. A coil of 400 μm external radius and 20 turns will generate for its part a field of 2.8 mT at 600 μm distance.

Two coils of 400 μm external radius, each having 5 concentric turns of 20 μm unit width, and deposited on the two faces of a substrate for example made of Kapton of 20 μm thickness, will also deliver around 1.5 mT at 600 μm. Generally speaking, the inducers are designed according to a pattern making it possible to deliver a magnetic field pulse B creating a sufficient electric field E in the target zone of the ganglionic neurons to excite, that is to say at a distance of 600 μm to 800 μm from said inducers in the case of a device intended to be implanted epi-sclerally according to one aspect of the invention. For a desired excitation at a height h of a circular planar coil, the external radius of said circular planar coil generating the electromagnetic pulse will be typically around h*√2, i.e. around 850 μm for an excitation at 600 μm and around 1100 μm for an excitation at 800 μm.

Figure 6A:
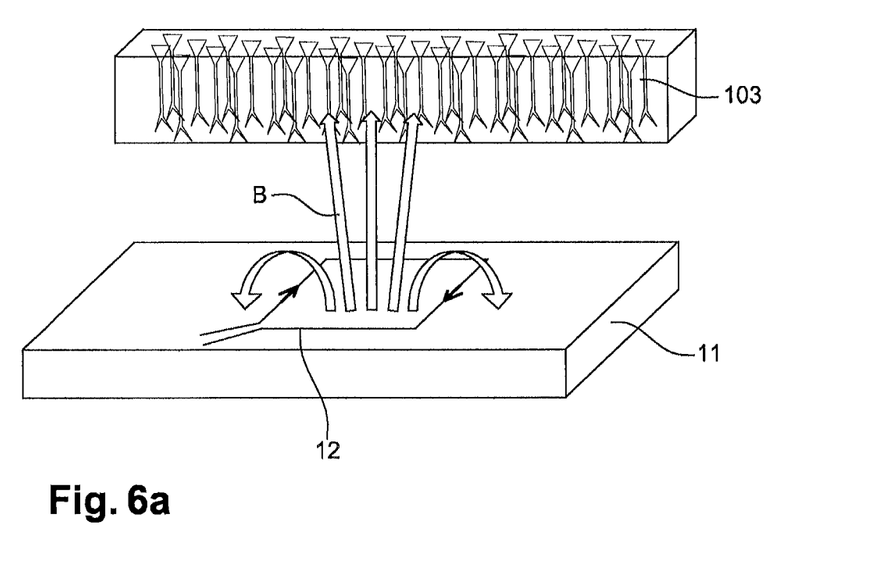
FIG. 6a schematically shows the operation of a device for prosthetic vision rehabilitation according to one aspect of the invention, comprising a single inducer.
Figure 6B:
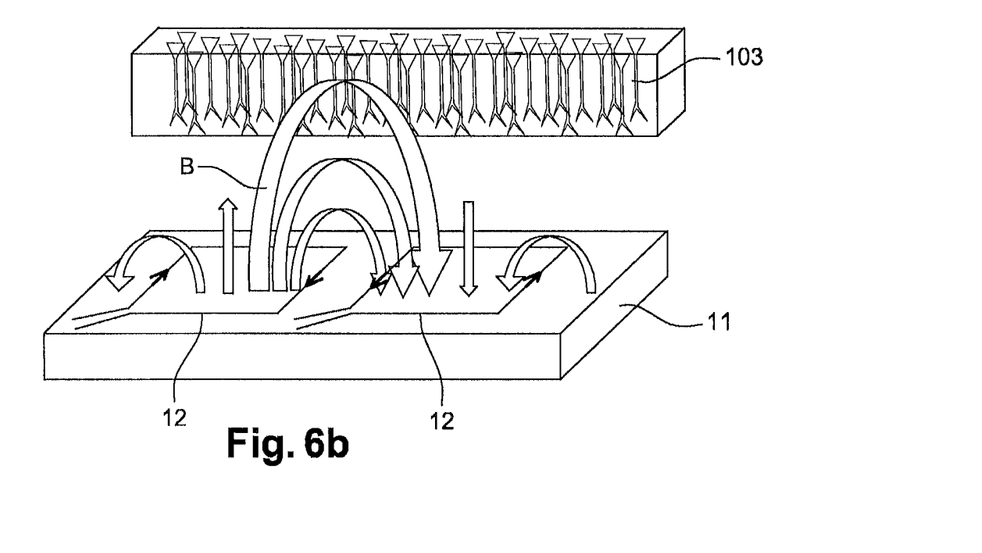
FIG. 6b schematically shows the operation of a device for prosthetic vision rehabilitation according to one aspect of the invention, comprising first and second inducers.

FIG. 6*a* schematically shows the operation of a device for prosthetic vision rehabilitation according to one aspect of the invention, comprising a single inducer. FIG. 6*b* schematically shows the operation of a device for prosthetic vision rehabilitation according to one aspect of the invention, comprising first and second inducers.

FIG. 6*a* shows a scleral explant 11 on which is arranged a single inducer 12 which is a single turn loop. A current pulse that flows in this single inducer 12 with single turn creates a magnetic field B making it possible to activate neurons 103 typically situated in the half-sphere above the turn 12, the magnetic field B being maximal at the middle of the turn 12.

FIG. 6*b* shows a scleral explant 11 on which are arranged two inducers 12, each inducer 12 being a single loop turn. The two inducers 12 are arranged in a same plane, on the surface of the substrate or support of the sclera explant 11, and are supplied by currents of opposite sense. The magnetic field B created by the flow of these currents of opposite sense is then maximal between the two turns 12.

The number and the arrangement of the inducers 12 thus make it possible to define precisely the zone that will be excited.

Figure 7A:
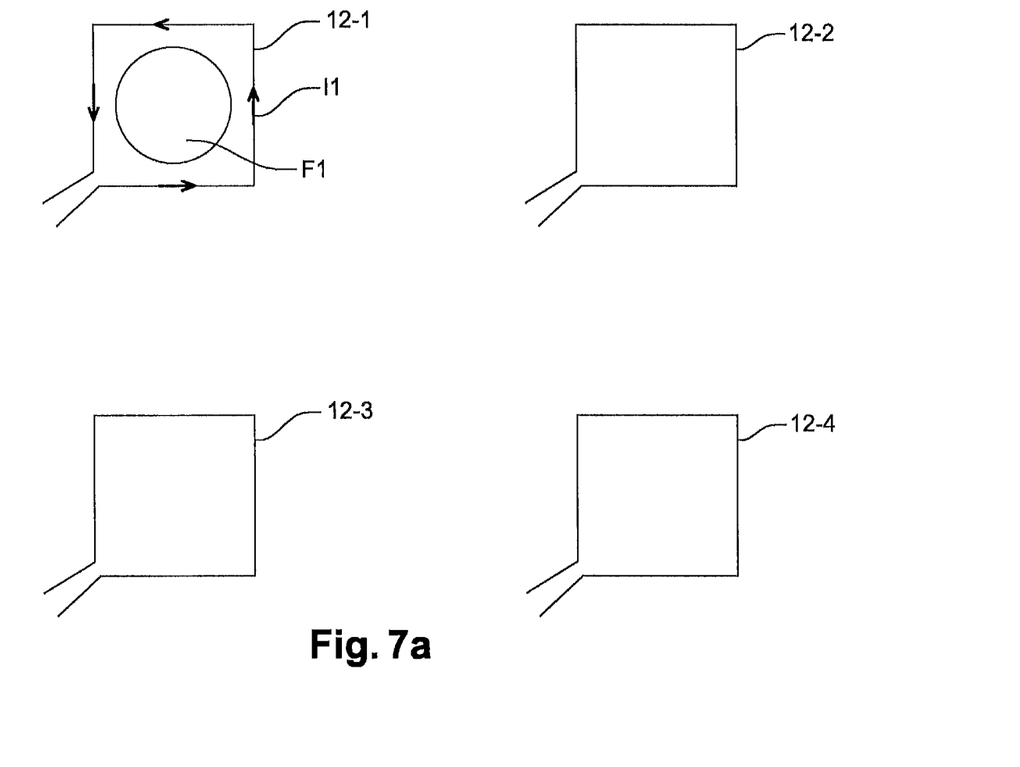
FIG. 7a schematically shows the magnetic field focal point obtained with a first configuration of an array of inducers.
Figure 7B:
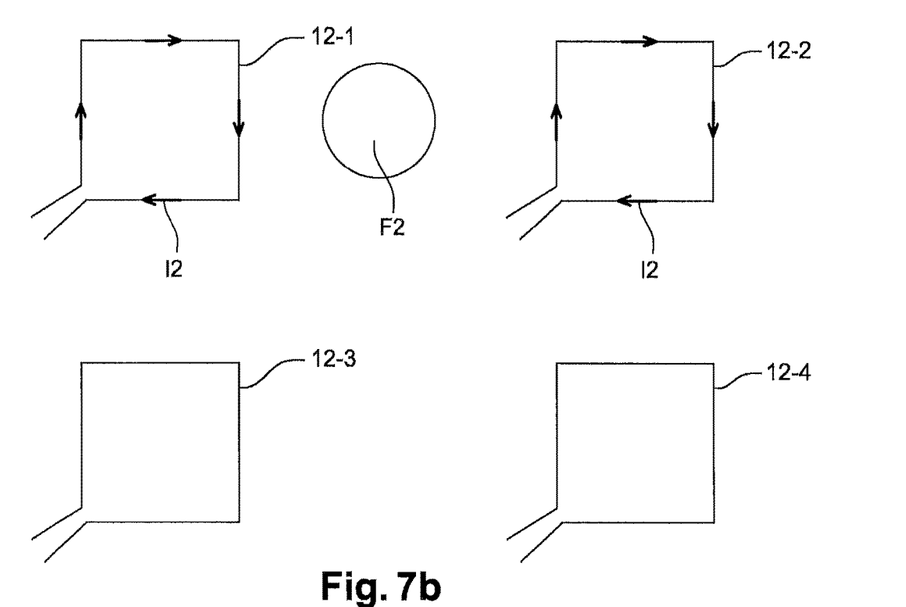
Figure 7C:
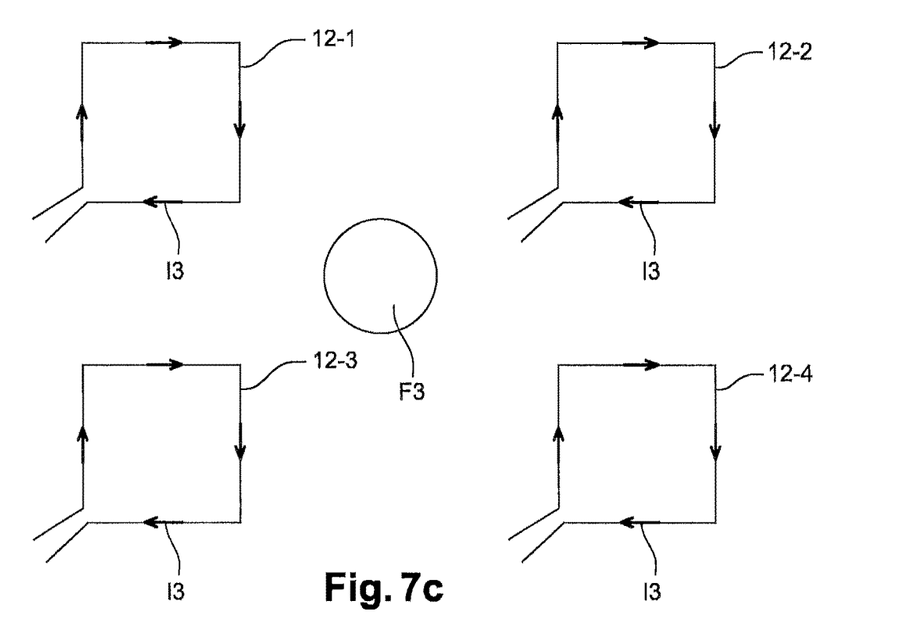

FIGS. 7*a*, 7*b* and 7*c* illustrate three configurations of a same array comprising a first inducer 12-1, a second inducer 12-2, a third inducer 12-3 and a fourth inducer 12-4, and the magnetic field focal point obtained for each configuration. The first, second, third and fourth inducers 12-1 to 12-4 are arranged in a square array. Each of the first, second, third and fourth inducers 12-1 to 12-4 is a single turn loop.

FIG. 7*a* shows a first configuration in which a single element of the array is supplied. In FIG. 7*a*, a first current I1 flows in the first inducer 12-1. No current flows in the second, third and fourth inducers 12-2, 12-3 and 12-4. The first current I1 is chosen to make it possible to reach the neuronal excitation threshold. In this first configuration, a magnetic field focal point F1 is obtained at the centre of the first turn 12-1. The maximum magnetic field is situated at the centre of the magnetic field focal point F1, pointing perpendicularly to the plane of the inducers, in the direction of the reader.

FIG. 7*b* shows a second configuration in which two elements of the array are supplied. In FIG. 7*b*, a second current I2 less than the first current I1 flows in the first inducer 12-1 and in the second inducer 12-2. No current flows in the third and fourth inducers 12-3 and 12-4. The second current I2 is not sufficient for the neuronal excitation threshold to be reached for each of the first and second inducers 12-1 and 12-2, considered individually. In contrast, the sum of the contributions of the second current I2 flowing in the first and second inducers 12-1 and 12-2 makes it possible to create a magnetic field focal point F2 reaching the neuronal excitation threshold. The magnetic field focal point F2 is obtained between the first inducer 12-1 and the second inducer 12-2.

FIG. 7*c* shows a third configuration in which the four elements of the array are supplied. In FIG. 7*c*, a third current I3 less than the second current I2 flows in each of the first, second, third and fourth inducers 12-1 to 12-4. The third current I3 is not sufficient for the neuronal excitation threshold to be reached for each pair of inducers considered individually, that is to say for the pair of the first inducer 12-1 and of the second inducer 12-2, the pair of the second inducer 12-2 and of the fourth inducer 12-4, the pair of the third inducer 12-3 and of the fourth inducer 12-4 and the pair of the first inducer 12-1 and of the third inducer 12-3. In contrast, the sum of the contributions of the third current I3 flowing in the first, second, third and fourth inducers 12-1 to 12-4 makes it possible to create a magnetic field focal point F3 reaching the neuronal excitation threshold. The magnetic field focal point F3 is obtained at the centre of the network formed by the first, second, third and fourth inducers 12-1 to 12-4.

FIGS. 6a and 6b on the one hand, and FIGS. 7a to 7c on the other hand thus clearly illustrate that, as a function of the inducers activated, zones of neuronal activation may be chosen, with a spatial specificity greater than that given uniquely by the design of turns of a single inducer.

Figure 8A:
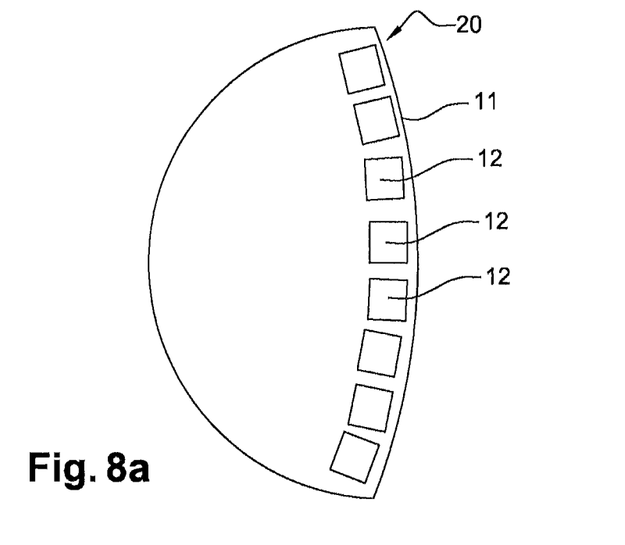
FIG. 8a schematically shows a first view of a device for prosthetic vision rehabilitation according to a second embodiment of the invention.
Figure 8B:
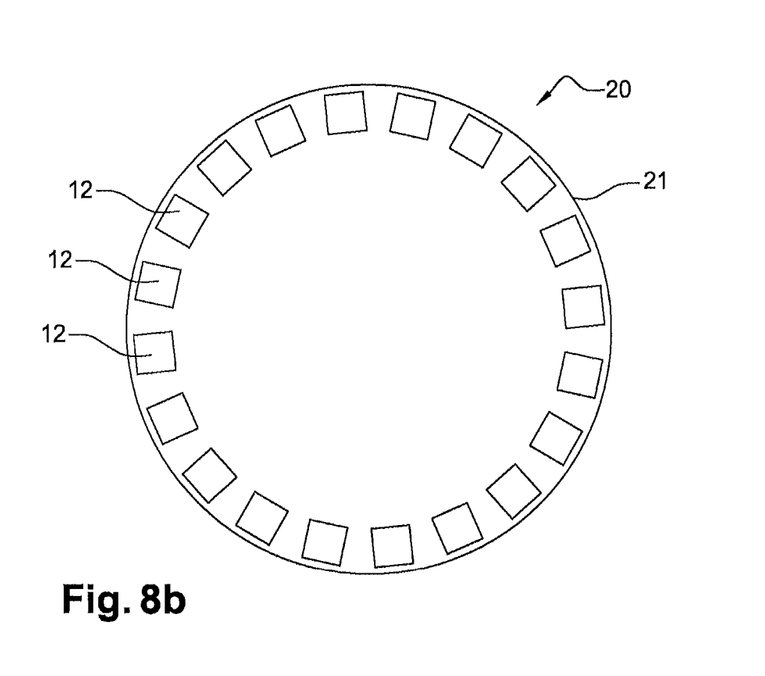
FIG. 8b schematically shows a second view of the device for prosthetic vision rehabilitation according to the second embodiment of the invention.

A second embodiment of the invention will now be described. FIG. 8a schematically shows a first side view of a device 20 for prosthetic vision rehabilitation according to the second embodiment of the invention. FIG. 8b schematically shows a second front view of the device 20 for prosthetic vision rehabilitation according to the second embodiment of the invention. FIGS. 8a and 8b are described jointly.

The device 20 for prosthetic vision rehabilitation according to the second embodiment of the invention comprises:
 a scleral explant or lens with scleral support or scleral lens 21, with a shape that is suitable for being in contact with at least one portion of the sclera of an eye, and
 a plurality of inducers 12 arranged on the scleral explant 21.

According to the second embodiment of the invention, the scleral explant 21 is suitable for being deposited in front of the eye, according to a mode of extra-ocular insertion not necessitating any surgical act. The inducers 12 are arranged on the periphery of the scleral explant 21 and are intended to act on ganglionic neurons on the outer periphery of the retina.

In the particular example illustrated in FIGS. 8a and 8b, the sclera explant 21 thus has a lens shape, the curvature of which is adapted to the natural curvature of the eye, and which may be deposited on the sclera surrounding the cornea. In an analogous manner to the scleral explant 11 described previously, the scleral explant 21 may be described as being a spherical calotte, the dimensions of which are chosen to enable the adaptation of the scleral explant 11 on an eye.

In an analogous manner to the description made previously in relation with FIG. 3, the scleral explant 21 comprises a substrate on the surface of which at least one inducer 12 is arranged, and an insulating layer that is deposited on the at least one inducer 12 and the portion of the substrate not covered by the at least one inducer 12. Examples of preferred materials for the substrate, for the at least one inducer and for the insulating layer as well as examples of manufacturing methods have been described previously in relation with FIG. 3.

Figure 9:
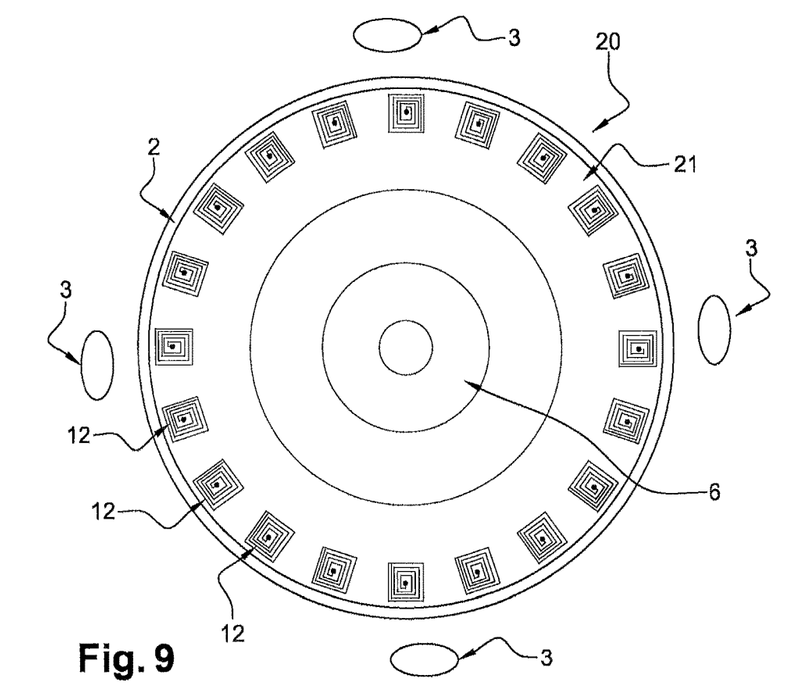
FIG. 9 schematically shows a view of the device for prosthetic vision rehabilitation according to the second embodiment of the invention, arranged in contact with a portion of the sclera of an eye.

FIG. 9 schematically shows a view of the device 20 for prosthetic vision rehabilitation according to the second embodiment of the invention, arranged in contact with a portion of the sclera 2 of the eye 1. FIG. 9 shows the sclera 2, the extra-ocular muscles 3 and the cornea 6 of the eye 1, the scleral explant 21 having a lens, or spherical calotte, shape, the curvature of which is adapted to the curvature of the sclera 2.

Figure 10:
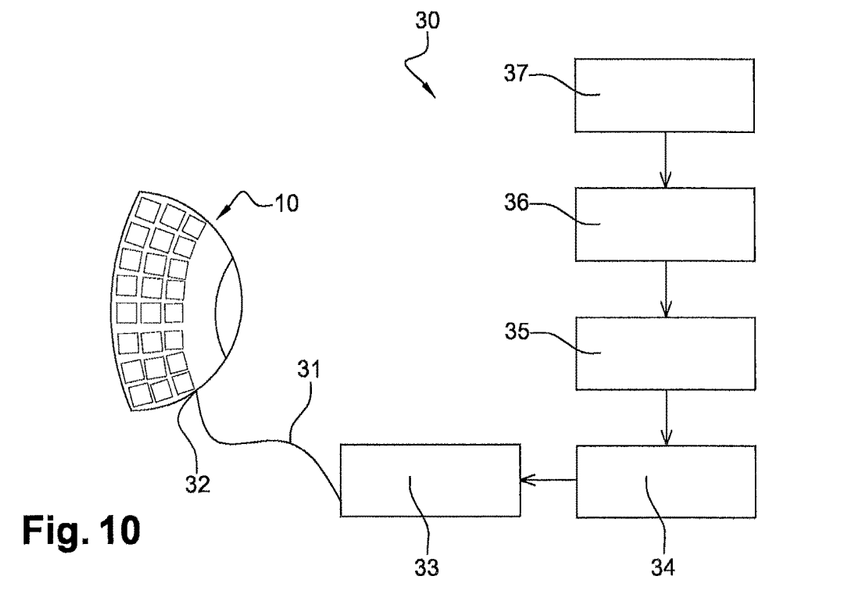
FIG. 10 shows a schematic representation of a system for prosthetic vision rehabilitation according to one aspect of the invention, using a device for prosthetic vision rehabilitation according to the first or the second embodiment of the invention.

FIG. 10 shows a schematic representation of a system 30 for prosthetic vision rehabilitation according to one aspect of the invention, comprising the device 10 according to the first embodiment of the invention. According to an alternative not represented in FIG. 10, the system 30 for prosthetic vision rehabilitation may comprise the device 20 according to the second embodiment of the invention, instead of the device 10 according to the first embodiment of the invention. The description that follows is thus also valid for a device 10 according to the first embodiment of the invention and for a device 20 according to the second embodiment of the invention.

FIG. 10 shows:
 a cable 31 comprising at least one connector 32 of an inducer 12, each inducer 12 preferentially having a connector 32, and the cable 31 preferentially comprising all the connectors 32 of the inducers 12;
 a multiplexer 33;
 a current pulse generator 34;
 a control unit 35 of the pulse generator 34;
 an image processing unit 36, and
 an image acquisition unit 37, or camera.

The image acquisition unit 37 carries out the acquisition of an image and transmits it to the image processing unit 36. The image processing unit 36 carries out an encoding of said image into numerical values corresponding to simplified pixels, as a function of the number of inducers. The encoding of the image is transmitted to the control unit 35. As a function of the encoding received, the control unit 35 sends a command signal to the current pulse generator 34. The generator 34 then sends at least one current pulse to the multiplexer 33. The multiplexer 33 then transmits the at least one current pulse to one inducer or to a plurality of inducers of the device 10 according to the first embodiment of the invention or of the device 20 according to the second embodiment of the invention, via the cable 31. The current pulses sent into the inducers 12 by the generator 34 may be of positive or negative polarity.

Each inducer 12 is preferentially connected to the current pulse generator 34 by a connector 32, preferentially produced in the same material as the inducer 12. The design of the connectors 32 is realised in order to minimise losses in the transmission line of each pulse, in order that the maximum power delivered is in the inducer 12. Impedance adaptation is thus an important parameter.

Each inducer 12 may be addressed individually. Alternatively, several inducers 12 may be addressed, for example to make it possible to obtain a magnetic field focal point with a precise positioning, as explained in relation with FIGS. 6a, 6b and 7a to 7c. In the case where several inducers 12 are addressed, or activated, the addressing may be carried out in one go or instead in several sequences. An addressing in several sequences notably makes it possible to limit heating of the inducers. In taking account of a rise time in the inducer, that is to say of the time necessary to pass from a zero current to a set point current in the inducer, of the order of 10 µs, and of a switching time of a standard multiplexer of the order of several µs, it is possible to activate sequentially 1500 to 2500 inducers, one by one, over a range of durations of 15 to 25 ms. This range of durations of 15 to 25 ms corresponds to a range of frequencies of 40 to 60 Hz, that is to say the fusion frequency beyond which the eye does not distinctly perceive two different signals. The value of the fusion frequency depends notably on the intensity of the modulation and the retinal eccentricity. In the case where capacitors are used, which discharge during the pulse, the charge time of these capacitors, of around 100 µs, is taken into account and it is then possible to activate sequentially 130 to 220 inducers, one by one, from 15 to 25 ms.

It is also possible to use current pulse trains of lower intensity, but making it possible by summation effect to reach a neuronal excitation threshold. In this case, the repetition frequency of the pulse trains is taken into account to calculate the total time required for the individual excitation of each inducer, and to calculate the maximum number of inducers that it is possible to excite over a duration of 15 to 25 ms. One advantage offered by the use of trains of current pulses of low intensity is the possibility of activating several inducers at the same time.

The invention claimed is:

1. A device for prosthetic vision rehabilitation, the device comprising:
   a scleral explant with a shape that is suitable for being in contact with at least one portion of the sclera of an eye;
   at least one inducer arranged on the scleral explant, and
   an insulating layer arranged on the at least one inducer, the at least one inducer constructed and arranged to create an electromagnetic field for neuronal stimulation of ganglionic neurons of the eye, the insulating layer galvanically insulating the at least one inducer from an excitation zone where the ganglionic neurons are located.

2. The device for prosthetic vision rehabilitation according to claim 1, wherein the scleral explant has a spherical calotte shape.

3. The device for prosthetic vision rehabilitation according to claim 1, wherein the scleral explant comprises a central portion and a peripheral portion surrounding the central portion, and wherein the at least one inducer is arranged on the peripheral portion of the scleral explant.

4. The device for prosthetic vision rehabilitation according to claim 1, wherein the scleral explant comprises an opening.

5. The device for prosthetic vision rehabilitation according to claim 4, wherein the scleral explant comprises a slit arranged between an external periphery of the scleral explant and the opening of the scleral explant, the slit defining two ends of the scleral explant being able to be moved apart from each other.

6. The device for prosthetic vision rehabilitation according to claim 5, wherein the scleral explant has a system for attaching the two ends of the scleral explant.

7. The device for prosthetic vision rehabilitation according to claim 1, comprising a plurality of inducers arranged on the scleral explant.

8. A system for prosthetic vision rehabilitation, the system comprising:
   an image acquisition unit;
   an image processing unit, receiving as input an image acquired by the image acquisition system and sending back as output an encoding of said image;
   a control unit, receiving as input the encoding of said image and sending back as output a command of a pulse generator;
   the pulse generator, sending according to the command of the control unit at least one pulse to a multiplexer;
   the multiplexer, transmitting the at least one pulse to at least one inducer or to at least one portion of a plurality of inducers of a device for prosthetic vision rehabilitation, the device for prosthetic vision rehabilitation comprising:
      a scleral explant with a shape that is suitable for being in contact with at least one portion of the sclera of an eye, and
      the at least one inducer arranged on the scleral explant.

* * * * *